United States Patent [19]

McGregor

[11] Patent Number: 5,116,313
[45] Date of Patent: May 26, 1992

[54] VARIABLE INTENSITY REMOTE CONTROLLED NEEDLELESS INJECTORS

[75] Inventor: Gavin McGregor, Gloucester, Canada

[73] Assignee: Her Majesty the Queen in right of Canada as represented by the National Research Council Canada, Canada

[21] Appl. No.: 576,609

[22] Filed: Aug. 31, 1990

[30] Foreign Application Priority Data

Aug. 31, 1989 [CA] Canada .................. 609988

[51] Int. Cl.$^5$ ............................ A61M 5/307
[52] U.S. Cl. .................................. 604/70
[58] Field of Search ...................... 604/68–72, 604/134, 135, 141, 150; 81/9.22

[56] References Cited

U.S. PATENT DOCUMENTS

| | | | |
|---|---|---|---|
| 2,695,611 | 11/1954 | Letac . | |
| 2,762,369 | 9/1956 | Venditty | 604/68 |
| 2,762,370 | 11/1956 | Venditty | 604/68 |
| 3,189,029 | 6/1965 | Stephens | 604/70 |
| 3,292,621 | 12/1966 | Banter . | |
| 3,424,154 | 1/1969 | Kinsley | 604/70 |
| 3,859,996 | 1/1975 | Mizzy et al. | 604/71 X |
| 3,910,266 | 10/1975 | Kawase | 604/68 |
| 4,031,783 | 6/1977 | Paul et al. | 81/9.22 |
| 4,059,107 | 11/1977 | Iriguchl et al. | 604/71 |
| 4,403,609 | 9/1983 | Cohen | 604/70 |
| 4,722,728 | 2/1988 | Dixon | 604/68 |
| 4,838,857 | 6/1989 | Strowe et al. | 604/67 |

FOREIGN PATENT DOCUMENTS

1069825 1/1984 U.S.S.R. ........................ 604/68

Primary Examiner—Edward M. Coven
Assistant Examiner—Sebastiano Passaniti
Attorney, Agent, or Firm—Eckert Seamans Cherin & Mellott

[57] ABSTRACT

An apparatus for injecting liquids into a body without using hypodermic needles, the liquid being ejected from a small orifice in a probe at a velocity which will penetrate the surface of a body against which the probe is placed. The apparatus ejects a specific small volume of the liquid under a very high initial velocity and pressure followed by the ejection of the main charge of liquid at a lower velocity so that the liquid flows into the channel caused by the initial penetration without penetrating to a greater depth. The probe is connected to a hand-held portion whose other end is attached via a flexible tube containing a suitable hydraulic fluid to two remote pressure intensifiers, one of which creates the required high initial pressure for a short period of time and the other of which provides the pressure necessary to eject the main charge of liquid at a lower velocity. The second intensifier is synchronized electronically or mechanically to follow the initial pulse when its pressure decays to the main charge injection pressure. The pressures created by the high pressure intensifier and second pressure intensifier are individually adjustable for various type of situations, such as depth of penetration or skin conditions.

21 Claims, 2 Drawing Sheets

VARIABLE INTENSITY REMOTE CONTROLLED NEEDLELESS INJECTORS

FIELD OF THE INVENTION

The invention relates to an apparatus for injecting liquids into a human or animal body, without the use of a hypodermic needle, in which the liquid is ejected from a nozzle with a small orifice that is held against the body. The apparatus ejects the liquid under a very high initial velocity and pressure for a short period of time, which limits the volume ejected, in order to penetrate the surface of the body to a specific depth. This is immediately followed by an ejection of the liquid at a lower velocity and pressure so that the liquid flows into a channel caused by the initial penetration without penetrating to a greater depth.

BACKGROUND OF THE INVENTION

Various types of needleless hypodermic injectors have been designed previously. These types have had a number of drawbacks such as being heavy, cumbersome and difficult to apply to regions of restricted access, a fact which limits their use in fields such as dentistry.

Many of the known devices are dependent on heavy springs, which are first pre-stressed and then trigger-released to drive a piston that applies pressure to a liquid in a chamber. The liquid is then ejected from the chamber through a restricted orifice. It has generally been recognized that these devices should initially produce a high pressure for a short time in order to create a high velocity jet which can penetrate the skin to a desired depth. This is followed by a lower velocity jet which injects the liquid through the pierced skin where it can disperse radially into the surrounding tissue without penetrating to a greater depth or cause further, unintentional, tissue damage. The velocity and pressure of the initial jet and the length of time it is applied determine the depth of penetration and how much pain is felt by the injection.

The known injectors have often used a double piston impactor arrangement in order to create the desired high initial pressure. A first piston is brought to a high velocity before impacting against a second piston to create a high initial impact pressure in that type of arrangement. The second piston applies this pressure to a liquid in a chamber so that the liquid is ejected through a small orifice in the chamber with an initial very high velocity. Other injectors have used a hydraulic fluid in a cylinder to force a piston against a spring so the spring is prestressed. A trigger mechanism is then used to activate a valve arrangement which initially releases a relatively large amount of hydraulic fluid from the cylinder for a short time followed by a slower rate of release of the hydraulic fluid from the cylinder. That spring driven piston is connected to a further piston which applies pressure to a liquid in another cylinder in order to eject that liquid from that cylinder through a small orifice. The relatively large amount of hydraulic fluid initially released provides a high initial velocity to the pistons followed by a slower movement during the slower release of the hydraulic fluid. Both types of devices create a loud noise during their operation which, in the first type is due to the first piston impacting against the second piston. The second type creates a loud noise when the relatively large amount of hydraulic fluid initially released is stopped and changed to a slower release of the fluid. This noise can frighten or distract a patient being injected. Furthermore, a mechanical blow is delivered to the patient by the apparatus which is in contact with the skin when the pistons reach the end of their stroke. This results in some physical shock.

U.S. Pat. No. 3,292,621 describes one type of jet injector inoculator which is operated with a $CO_2$ cartridge. This injector is designed to be operated with a particular type of ampule which is filled with inoculant, the ampule having a closure wall terminating in a nipple with a small orifice at one end The other end of the ampule is closed by a rubber piston. This ampule is inserted into and held in an opening at one end of the injector. The injector contains a piston in a cylinder with a ram extending from one side of the piston, the ram being aligned with the axis of the cylindrical ampule and having an end which is slightly spaced from the rubber piston in the ampule. A valve arrangement is used to apply $CO_2$ pressure against the piston which initially does not move due to the end of the ram being held with "a snap ring. The snap ring has a circular cross-section and is located in a groove in a wall adjacent to the end of the ram. As the $CO_2$ pressure builds up against the piston and reaches a predetermined level, the ram forces the ring outwardly, radially beyond the surface of the ram, and further into the groove. This releases the ram which then impacts on the rubber piston creating a high initial pressure in the ampule to eject the inoculant from the orifice at a high initial velocity. This is followed by the ram being pushed further into the ampule by the expanding gas behind the piston with the inoculant being ejected at a much lower velocity. This jet type inoculator has the same, previously mentioned, disadvantages as well as requiring a particular type of ampule.

U.S. Pat. No. 4,059,107 describes another type of injector with a first piston fitted into a first cylinder at one end of its housing. A rod extends between the first piston and a second piston which fits into a second cylinder at the other end of the housing. The second cylinder forms a liquid medication containing chamber which has a smaller diameter than the first cylinder to which it is joined by a stepped portion. A spring is located in the first cylinder between the piston and one end of the housing. Oil is inserted, at high pressure, through a check valve into the first cylinder on the side of the first piston opposite to the spring to prepare this injector. This forces the first piston towards the one end against the pressure created by the spring, which prestresses the spring. It also moves the second piston in the same direction creating a vacuum in the liquid medication chamber, which draws liquid medication from a vial, through a check valve, into the chamber. A cap with a nozzle having a small hole closes an end of the chamber and a check valve between the hole and chamber prevents air being drawn into the chamber when it is being filled.

A duct with a check valve is connected to the part of the first cylinder containing the oil. This duct leads to a third cylinder in which a third piston is spring-biased towards the end of the third cylinder connected to the duct. The third piston contains a small opening. A trigger mechanism is connected to the check valve in the duct and, when activated, opens that check valve to allow oil from the first cylinder to flow into the third cylinder, which forces the third piston towards the opposite end of the third cylinder.

This allows the pre-stressed spring to impart a high initial velocity to the first piston as the oil pressure in the first cylinder falls quickly until the third cylinder is full of oil. The third piston contains a small opening, and when the third cylinder is full, the piston being at opposite end of the third cylinder, oil flows through that opening. At that point, oil flows out through the opening in the third piston so that the oil pressure in the first cylinder falls at a slower rate resulting in a slower motion of the first piston. The interconnection of the first and second pistons creates the desired high initial pressure and ejecting velocity for the medication, followed by a lower ejecting velocity.

The same previously mentioned disadvantages exist with this type of design. A loud noise is created during operation, in this case by the third piston reaching the opposite end of the third cylinder, which stops the initial rapid fall of oil pressure in the first cylinder. This patent also suggests several alternative designs that can create a high initial pressure for the medication to pierce the skin followed by the injection of the medication through the pierced skin at a lower pressure. Both U.S. Pat. Nos. 4,059,107 and 3,292,621 are directed to portable hand held injectors.

U.S. Pat. No. 3,424,154 describes another type of apparatus for jet injection of fluids into soft tissues of a living body, in which a hand-held injection portion is connected via a flexible tube to a remote pneumatic motor. The hand-held portion consists of a probe terminating in a minute orifice from which a high-velocity jet of liquid may be ejected by movement of a piston inside the hand-held portion. The piston is activated by a liquid column in the flexible tube, which is connected to the pneumatic motor. The pneumatic motor includes a first piston and an auxiliary piston in a cylinder, the auxiliary piston being spring-biased away from the first piston, but moveable under the influence of fluid pressure to strike a hammer blow against the first piston. The fluid pressure then moves both pistons, and a further piston, which is connected to the first piston and contacts the liquid column, in a direction which will apply pressure to the liquid column. This will move the piston in the hand-held portion to create a jet of liquid from the probe. This apparatus, due to the auxiliary piston impacting against the first piston, emits a very high initial velocity jet followed by a much lower velocity jet. The apparatus described in U.S. Pat. No. 3,424,154 has a number of advantages over previous devices in that the pneumatic motor can be screened from the patient and the stopping of its pistons at the end of their stroke will not deliver a physical shock to the hand-held portion.

All of the previously mentioned devices have the limitation that the initial pressure and the pressure creating the lower velocity jet are determined by the dimensions and characteristics of the apparatus, and as a result are not readily adjustable. It is difficult to adjust the pressures of these devices to suit various skin conditions. For example, it may be possible to set a pressure which will painlessly penetrate the skin of a human or animal, but it is difficult to limit the depth of penetration and at the same time control the rate and volume of discharge. These difficulties may cause unintentional tissue damage and trauma.

SUMMARY OF THE INVENTION

It is an object of the invention to provide an improved apparatus for injecting liquids into a body from a nozzle having a restricted orifice which is held against the surface of the body, the apparatus ejecting the liquid under a very high initial velocity and pressure for a short period of time in order to penetrate the surface of the body, followed by an ejection of the liquid at a lower velocity so the liquid flows into a channel caused by the initial penetration without penetrating to a greater depth, the pressures generated by the apparatus being adjustable.

It is a further object of the invention to provide an apparatus, in which the time duration and pressures required for the initial high velocity jet and following low velocity jet are adjustable. The ability of the apparatus to control the initial penetration action as well as the diffusion rate solves many difficult injection problems.

It is still a further object of the invention to provide an apparatus for dentistry, which is needleless, easily used, readily adjustable and capable of injecting the large volumes of anesthetic required for dental work.

An injector, according to a preferred embodiment of the invention consists of a slim hand-held portion with an attached probe having a restricted orifice in a tip at its free end, the hand-held portion's other end being connected to a flexible tube containing hydraulic fluid, a first cylinder in the probe communicating with the orifice and a first piston being movable in the first cylinder under the influence of a second piston to which the first piston is connected, the second piston being movable in a second cylinder in the hand-held portion which is co-axial to the first cylinder, the second piston being spring-biased towards said other end which is in communication with the hydraulic fluid in the tube, the flexible tube being connected to two remote pressure intensifiers; wherein a first high intensity pressure intensifier is provided with a first adjustable drive system to provide a high initial pressure pulse through the hydraulic fluid to said second piston and a second low pressure intensifier consists of a third cylinder containing a third piston which is in contact with the hydraulic fluid, the third piston being movable by a second adjustable drive system to transfer pressure via the hydraulic fluid to the second piston.

In a further preferred embodiment, the first pressure intensifier consists of a first plunger and a fourth piston in a fourth cylinder, with the first plunger being movable by the first adjustable drive system so it can provide an impact to the fourth piston which is in contact with the hydraulic fluid to provide said high initial pressure pulse.

In a still further preferred embodiment, the third piston is connected to a second plunger and the first and second adjustable drive systems are first and second solenoid coils which are associated with the first and second plungers respectively, the first and second plungers consisting of magnetic material with currents applied to the first and second solenoid coils being adjustable.

BRIEF DESCRIPTIONS OF THE DRAWINGS

Other objects, advantages and features of the invention will become more readily apparent from the following detailed description of a preferred embodiment taken in conjunction with the accompanying drawings, wherein.

DESCRIPTION OF THE PREFERRED EMBODIMENT

Figure 1:
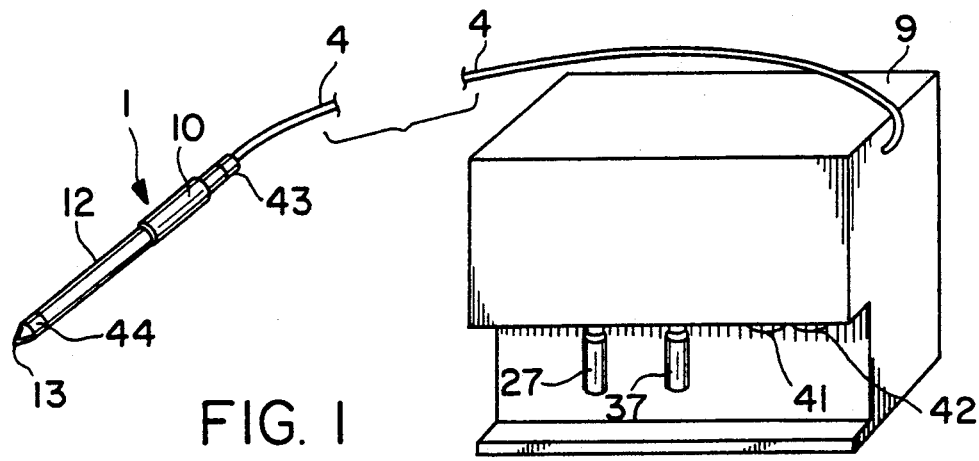
FIG. 1 is a perspective view of the hand-held portion of the injector according to the present invention and a remote control cabinet.

FIG. 1 shows a slim hand-held portion 1 of an injector according to the invention which is attached, at one end, to a high pressure flexible cable 4 which goes to a cabinet 9 containing pressure intensifiers.

The other end of the hand-held portion 1 contains a restricted orifice 13 through which medication can be ejected The cabinet 9 is provided with adjustments 27, 37, 41 and 42 to control the pressures and velocity with which medication is ejected.

Figure 2:
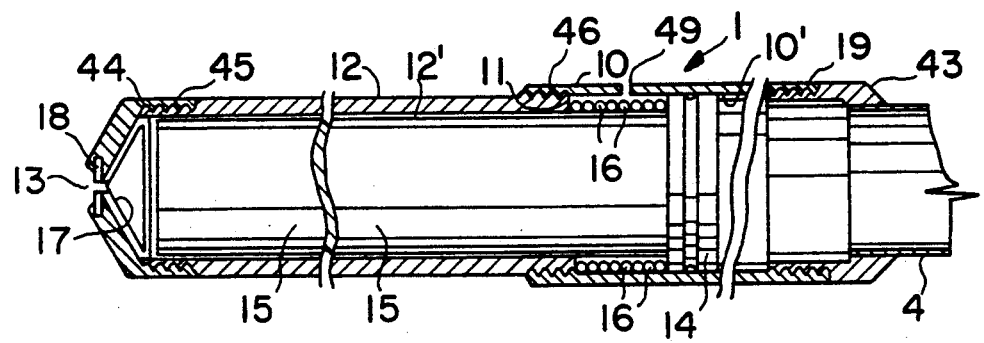
FIG. 2 is an enlarged longitudinal sectional view of the hand-held portion of the injector.

Hand-held portion 1 consists of a slim hand-held tubular body 10 with an inner cylinder 10' connected to and co-axial with a slimmer probe 12 having an inner cylinder 12' as shown in FIG. 2. The co-axial cylinders 12' and 10' communicate with each other and are joined together by a stepped portion 11. The end of probe 12 is attached to a tip portion 44 which contains a small orifice 13 through which liquid, such as medication, in cylinder 12' can be ejected by a piston 15, which is movable in cylinder 12'. Piston 15 is integral with an elongated piston rod which is co-axial with and solidly connected to a further piston 14, which is movable in cylinder 10'. A spring 16, located between the stepped portion 11 and piston 14, biases the piston 14 towards the opposite end of cylinder 10' away from cylinder 12'. The inner surface of tip portion 44 adjacent the orifice 13 has a conical surface of the same shape as the conical shaped end 17 of piston 15 so that essentially all of the liquid in the probe 12 is ejected as the piston 12 moves towards the orifice 13.

The restricted orifice 13 is formed by an approximately 0.125 mm diameter opening in a sapphire disk 18 which is centrally embedded in the front part of tip portion 44. The central inner part of the sapphire disk at the area of orifice 13 has a conical shaped indentation which conforms in shape to the central conical tip 17 of the piston 15. The surface of this conical indentation blends smoothly with and is an extension of the inner conical surface in tip portion 44. The tip portion 44 is attached to the probe 12 by a threaded connection 45 and probe 12 is attached to the hand-held body 10 by a threaded connection 46.

Thus the probe 12 is easily disconnected for sterilization purposes and allows the apparatus to be quickly and easily adapted for different types of liquids or medications.

The other end of tubular body 10 is connected to a high pressure flexible tubing 4 by a threaded connection 19. The tubing 4 has an enlarged end 43 with a outer threaded surface which is threaded into an inner threaded end of tubular body 10. Hydraulic fluid, such as water or mineral oil, in tubing 4 is then in contact with piston 14 in cylinder 10'. When pressure is applied to the hydraulic fluid, piston 14 is forced away from end 43 against the bias applied by spring 16. Piston 15 is also pushed in cylinder 12' towards orifice 13, which results in any liquid in cylinder 12' being ejected through orifice 13. Vent 49 in body portion 10 prevents air pressure from being built up between stepped portion 11 and piston 14.

Figure 3:
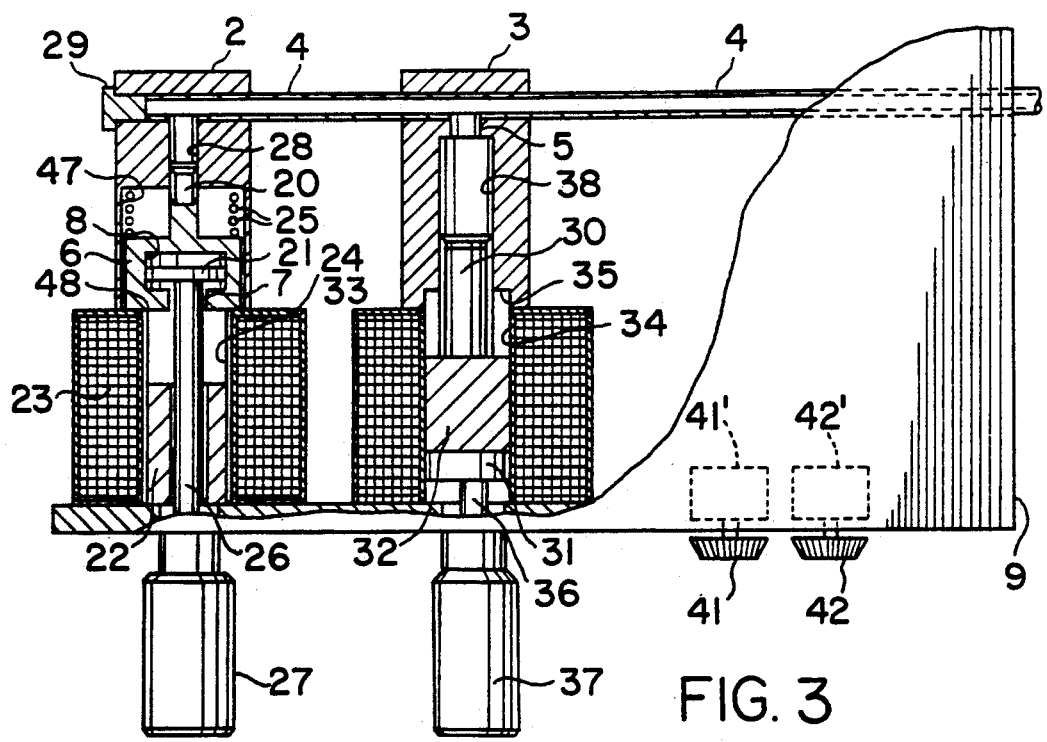
FIG. 3 is a view of part of the remote control cabinet with a portion being broken away to show pressure intensifiers in cross-section.

The other end of flexible tubing 4 is connected to a first high intensity (impact) pressure intensifier 2 by a T-connection and to a second low pressure intensifier 3 by a further T-connection, as shown in FIG. 3. These elements of the apparatus, along with further elements if desired, can be screened from the field of view of a patient and located in a sound-absorbing enclosure (cabinet 9), so that any noise created by impact pressure intensifier 2 and pressure intensifier 3 is attenuated to a degree which will not disturb the patient. The sound-absorbing enclosure 9 can also serve as a control console for the apparatus.

The high pressure intensifier 2 contains a small piston 20 which is movable in a small cylinder 28, one end of which is in communication with flexible tubing 4 via a T-connection One end of that T-connection to tube 4 is closed by an end plug 29. With plug 29 removed, hydraulic fluid can be inserted into the apparatus. The other end of this T-connection is connected to tube 4 that leads to a further T-connection at low pressure intensifier 3. The other end of cylinder 28 opens into a larger co-axial cylinder 47, in which a further piston 6 is located, piston 20 being solidly connected to piston 6. Cylinder 47 opens into a slightly smaller co-axial cylinder 24 with a step portion 48 joining one end of cylinder 47 to cylinder 24. A spring 25 located between the other end of cylinder 47 and piston 6, biases piston 6 towards the step portion 48.

Solenoid coils 23 surround an upper part of cylinder 24 in which an annular cylindrical plunger 22 of magnetic material is located. Coils 23 and plunger 22 form a solenoid, with plunger 22 being spaced from piston 6 by a gap "g". The current which can flow in the solenoid coils 23 is adjustable by means of a potentiometer 41' and control knob 41. When current is applied to coils 23, this draws plunger 22 upward until it impacts against piston 6 and forces piston 20 upward with a high initial velocity. The force of the impact is determined by the current in coils 23 and the gap "g". An opening, not shown, prevents excessive air pressure build-up between plunger 22 and piston 6.

Piston 6 contains a cavity 8 with an opening 7 which faces cylinder 24, the width of opening 7 being smaller than that of cavity 8. An adjustment rod 26 extends through opening 7 and has an enlarged base 21, which fits inside cavity 8. The base 21 is larger than opening 7, so that piston 6 can only travel upward until the base 21 contacts the bottom of cavity 8. The rod 26 extends through the bore of cylindrical plunger 22 and is connected to a micrometer adjustment arrangement 27 which can be used to determine the rest position of base 21 in cavity 8. This determines the distance that piston 6 can move upward when impacted by the cylindrical plunger 22 and, as a result, provides a stroke control adjustment for the high pressure intensifier 2. This determines the amount of hydraulic fluid displaced by piston 20 which, in turn, determines the amount of liquid ejected through orifice 13 in probe 1 by the initial high pressure pulse generated by the plunger's 22 impact. The amount of liquid ejected and the velocity at which it is ejected determine the depth of penetration of the liquid into a body.

Spring 25 cushion the impact of piston 6 against base 21 and then returns piston 6 so that it rests against the step portion 48 between cylinders 47 and 24 when current is removed from solenoid coils 23.

The low pressure intensifier 3 is also connected to flexible tube 4 by a further T-connection. This low pressure intensifier contains a cylinder 38 which is in communication with said further T-connection at 5. Cylinder 38 is co-axial with and opens into a larger cylinder 34 containing a plunger 32 of magnetic material. A piston 30 is movable in cylinder 38 and is attached to plunger 32. Solenoid coils 33 surround cylinder 34 and co-operate with plunger 32 to form a solenoid.

The amount of current that flows in coils 33 is determined by a potentiometer 42' and control knob 42. This current can pull plunger 32 upward along with piston 30, and as a result determines the pressure and velocity at which liquid is ejected through orifice 13 in probe 1 after the initial high pressure pulse. The pressure and velocity at which the low pressure intensifier ejects liquid from orifice 13 is readily adjustable by potentiometer 42'.

Plunger 32 rests on a base 31 which is attached to an adjustment rod 36. The adjustment rod 36 is connected to a micrometer adjustment arrangement 37, which is used to determine the height of base 31 and position of piston 30 in cylinder 38. This determines the length of stroke that piston 30 can travel. That, in turn, determines the amount of liquid ejected from cylinder 12' in hand-held portion 1 and the total amount of, for example, liquid medication administered.

To operate the injector, the flexible pipe 4 is first completely filled with hydraulic fluid while ensuring there is no air in the system. Current is then applied to solenoid coils 33 to force piston 30 upward inside cylinder 38, which through the hydraulic fluid, applies pressure to piston 14, thereby moving it and piston 15 in cylinder 12' to a position where the tip 17 engages the inner conical surface at orifice 13. The tip of probe 12 and orifice 13 is then brought into contact with a liquid, such as medication to be administered, and current is applied to the solenoid coils 33 in order to draw plunger 32 and piston 30 back. This creates a drop in pressure, which allows spring 16 to move piston 14 away from stepped portion 11, drawing piston 15 away from the orifice 13 and creating a vacuum in cylinder 12'. The vacuum draws the liquid through orifice 13 into cylinder 12'. A suitable adapter for the nozzle tip for use with a serum bottle is shown in FIG. 4.

Once the required amount of liquid has been withdrawn into cylinder 12', the apparatus is ready to inject that liquid into a body. The amount of liquid can be determined by adjusting base 31 and position of plunger 32, and 5 hence the amount of stroke which piston 30 has in cylinder 38. The required current intensity to be applied, the length of duration and time applied are set in a control system (not shown) for coils 23 and 33. In addition, the stroke of piston 6 is adjusted by arrangement 27, which determines the amount of liquid ejected by the initial high pressure pulse and the depth of penetration.

The current to be applied to coils 23, adjusted by potentiometer 41', determines the initial high impact pressure applied by piston 20 to the hydraulic fluid. The probe 12 is then placed against the skin of a body to be injected, and the device is activated by either a switch on the hand-held portion 1 or a footpedal switch, which switches are connected to the control system. Once activated, the predetermined currents are applied to the coils so the liquid in cylinder 12' is ejected through orifice 13 with a predetermined high initial velocity created by piston 20 and coils 23, followed by an ejection with a lower velocity and pressure as determined by piston 30 and coils 33. The pressures used are adjusted to optimize the type of injection for various types of situations. Although the apparatus has been described mainly with reference to the injection of medication, it can also be applied to other areas such as tattooing and the marking of meat product etc. In the case of tattooing, the pressure intensifiers can be programmed to provide a multiple of very short sharp pulses which are only of sufficient strength to penetrate through the skin. A further embodiment of the invention which can be easily adapted to tattooing is shown in FIG. 5.

Figure 4:
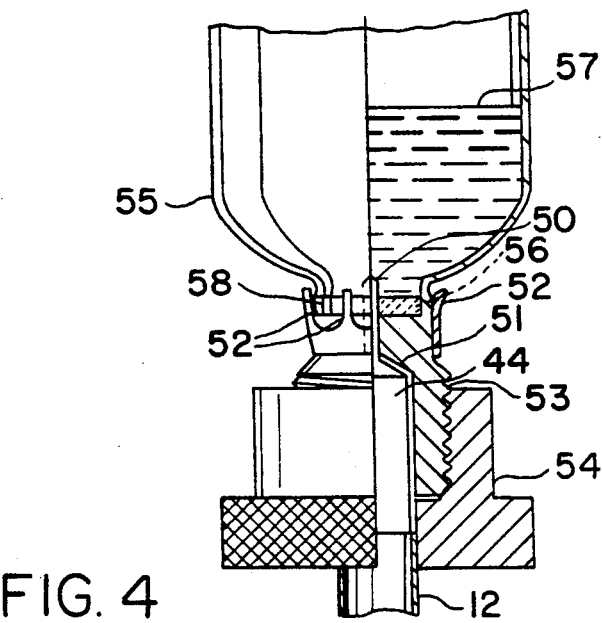
FIG. 4 is a view which illustrates, partly in cross-section, an attachment for filling the hand-held portion with liquid medication.

FIG. 4 illustrates one type of adapter which maybe used with the apparatus in order to fill the chamber 12' with medication 57 from a serum bottle 55. The adapter consists of a hollow needle 50 with an integral cap 51 at one end which fits over the end of the probe 12, the opening in the hollow needle being aligned with and communicating with the orifice 13. The needle and cap are embedded in split collet 53 having a central cylindrical opening extending outward from the cap S1 towards one end of collet 53, the opening having a size in which the end of probe 12 fits so that cap 51 is aligned with tip portion 44 of probe 12. The needle 50 extends outwardly past the other end of block 53.

The adapter also has integral flexible fingers 52 which extend from the split collect 53 in the same direction as the needle, the fingers having hooks at their free end. The split collet 53 is externally threaded at the end in which probe 12 fits with an internal threaded collet 54 being threaded onto the split collet 53. To use the adapter, the end of probe 12 is inserted into the cylindrical opening and the needle is used to penetrate the rubber seal 56 of a serum bottle 55 with said other end of collet 53 resting against the rim 58 of bottle 55. The collet 54 is threaded further onto 53 so as to clamp probe 12 in the collet 53. The flexible fingers 52 press against the rim so that their hooks engage around the rim 58 of the bottle and firmly hold it in place against collet 53. The probe 12 can then be readily filled by creating a vacuum in cylinder 12, which withdraws medication from the bottle 55 through the hollow needle 50, through the orifice 13 in tip portion 44 and into cylinder 12'.

Figure 5:
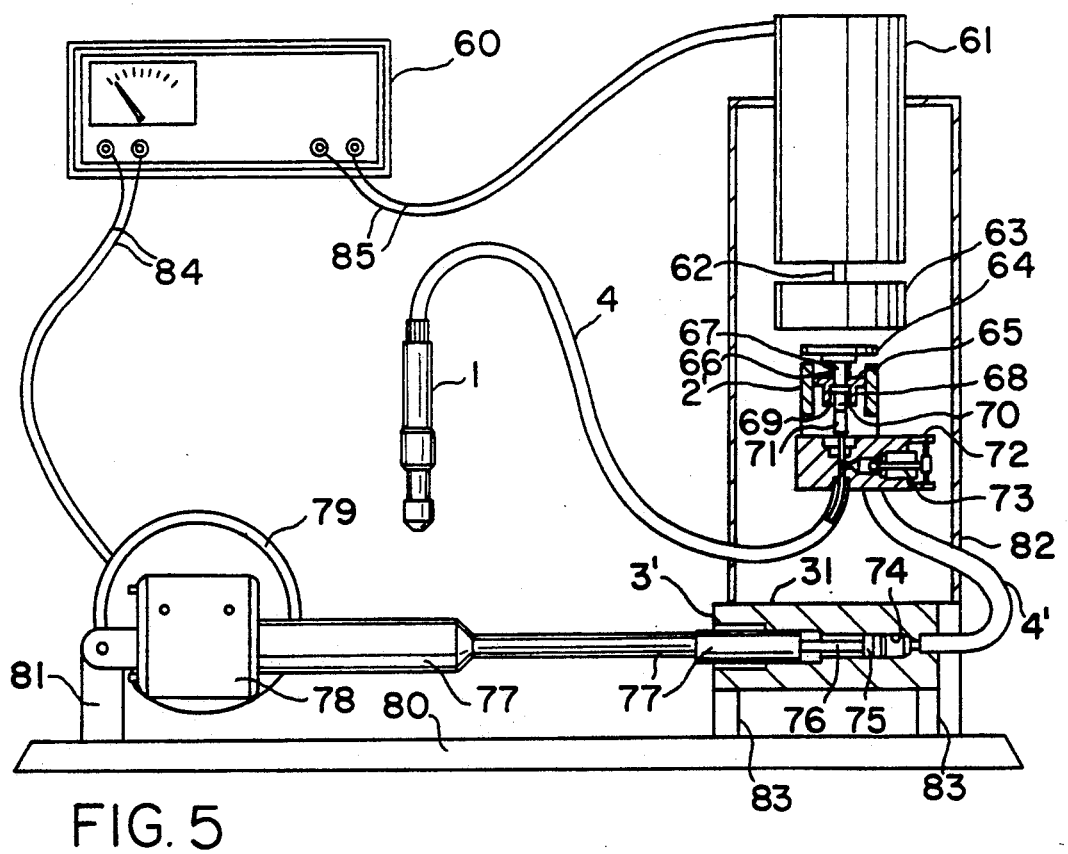
FIG. 5 is a view which illustrates, partly in cross-section, a further embodiment of the invention.

FIG. 5 illustrates a further embodiment of an injector according to the present invention wherein an adjustable power supply and controller 60 supplies drive currents to a solenoid 61 by leads 85 and to a rotary electric motor 79 by leads 84. The rotary motion of motor 79 is converted into linear motion by a gear transmission system 78, which is connected to drive rods 77 to provide a linear actuator for piston rod 76 and piston 75 inside of cylinder 74. Cylinder 74 and piston 75 form a low pressure intensifier 3', which can provide a high volume stroke of about 2 c.c., and create a pressure of from 200 to 2000 p.s.i. at the orifice in hand-held probe 1. Hydraulic fluid in cylinder 74 is in communication with fluid in tube 4' and, through a return flow check valve 73 in junction block 72, with high pressure tubing 4, which is connected to hand-held portion 1 so that pressure created by piston 75 is transferred to hand-held portion 1. The drive current for motor 79 is adjustable and provides a means by which the low ejection pressure at the orifice in hand-held portion 1 can be adjusted.

A further inlet to the (T) junction block 72 is connected to the outlet of a high pressure low volume cylinder 71 in high pressure intensifier 2'. A piston 70 inside cylinder 71 is connected to a piston rod to which an enlarged section 68 is attached, section 68 being movable in a cavity 69 above cylinder 71.

The cavity 69 is formed by a recess in the top of the block containing cylinder 71 and a top cover 65. A rod 67, which is an extension of the piston rod above enlarged section 68, extends upward through a central opening in cover 65 and is connected to a platform 64.

The movement of piston 70 in cylinder 71 is limited by the movement of enlarged section 68 in cavity 69 whose bottom surface forms a stop to limit the movement of section 68 downward while the top cover 65 forms a stop to limit the movement of section 68 in the other direction. The drive for the high pressure is formed by a weight 63 spaced a short distance above platform 64, weight 63 being attached to a drive rod 62 of solenoid 61.

Drive current to solenoid 61 can be adjusted so that weight 63 delivers a single sharp impact to platform 64 which drives piston 70 downward, creating an initial high pressure pulse which is transferred via hydraulic fluid in cylinder 71 through the "T" connection in junction block 72 and high pressure tubing 4 to hand-held portion 1. Depending on the current applied by controller 60 to solenoid 61, an initial high pressure pulse of between 5000 to 15000 p.s.i. is created at the orifice in the probe of hand-held portion 1.

The return flow check valve 73 prevents hydraulic fluid in tubing 4 from contacting hydraulic fluid in tube 4' during the initial high pressure pulse, which has only a short duration. Then the linear actuator, formed by transmission system 78 and drive rods 77, is able to drive piston 75 in cylinder 74, forcing hydraulic fluid through check valve 73 to tubing 4, thereby creating a low pressure ejecting force at the orifice of between 200 to 2000 p.s.i.

Alternatively, the solenoid 61 can be supplied with drive currents from controller 60, which creates a reciprocating motion of weight 63 providing a rapid series of impacts of weight 63 against platform 64.

This provides a rapid series of high pressure pulses at the orifice, with a spring 66 between platform 64 and top cover 65 returning platform 64 to its rest position between pulses. The spring 16 in hand-held portion 1, as shown in FIG. 2, also tends to return platform 64 to its rest position. Piston 75 can supply hydraulic fluid at a low pressure through check valve 73 to high pressure tubing 4 between the pulses created by solenoid 61. This series of high pressure pulses, which can be adjusted to provide a pressure at the orifice which will eject liquid at a velocity that will just penetrate the surface of the skin, can be used for tattooing.

The return flow check valve 73 can be manually operated to form a path allowing hydraulic fluid to be returned from hand-held portion 1 and tube 4 through tube 4' to cylinder 74. In this manner, piston 75 can be withdrawn back into cylinder 74, and that action can be used to refill the probe with medication or other liquid as previously described.

Various modifications may be made to the preferred embodiment without departing from the spirit and scope of the invention a defined in the appended claims.

For instance, although one preferred embodiment has been described with solenoid drives for the high pressure (impact) intensifier and low pressure intensifier, other types of drive systems may be employed, such as air or hydraulic cylinders. However, the use of electrically operated solenoids permits the control system to be electronically programmed by incorporating a microprocessor to compute dose rates and the pressures which may be required for various applications. The time during which the low pressure intensifier is activated may be a preset time after activation of the high pressure intensifier, or it may be synchronized electronically to follow the initial pulse when its pressure decays to the main charge injection pressure. In the latter case a pressure determination device can be incorporated into the system.

I claim:

1. An apparatus for injecting liquid into a body through a penetrable skin thereof, comprising a slim hand-held portion having a restricted orifice in a tip at its free end and its other end connected to a high pressure flexible tube containing hydraulic fluid, said flexible tubing being connected to remote pressure intensifier means, said hand-held portion comprising a first cylinder within said hand-held portion communicating with said orifice, a first piston movable in said first cylinder, movement of the first piston towards said orifice ejecting any liquid placed in the first cylinder out through the orifice, a second cylinder in said hand-held portion co-axial with said first cylinder, a second piston movable in said second cylinder and connected to said first piston, the second piston being spring-biased towards said other end and communicating with the hydraulic fluid in said flexible tube; and said remote pressure intensifier means comprising a first high pressure intensifier provided with a first adjustable drive system to provide a high initial pressure pulse through the hydraulic fluid to said second piston and a second low pressure intensifier consisting of a third cylinder containing a third piston which is in contact with the hydraulic fluid, the third piston being movable by a second adjustable drive system to transfer a low secondary pressure via the hydraulic fluid to the second piston.

2. An apparatus as defined in claim 1, wherein said pressure intensifiers are located in a sound absorbing enclosure.

3. An apparatus as defined in claim 2, wherein the first high pressure intensifier consists of a first plunger and a fourth piston in a fourth cylinder with the first plunger being movable by the first adjustable drive system so it can provide an impact to the fourth piston providing said high initial pressure pulse.

4. An apparatus as defined in claim 3, wherein the third piston is connected to a second plunger and the first and second adjustable drive systems are first and second solenoid coils which are associated with the first and second plungers respectively, the first and second plungers consisting of magnetic material with currents applied to the first and second solenoid coils being adjustable.

5. An apparatus as defined in claim 4, wherein a mechanical arrangement is included to adjust the rest position of the second plunger and thereby the third piston in the third cylinder, which provides a predetermined maximum stroke for the third piston in the third cylinder.

6. An apparatus as defined in claim 5, wherein the fourth cylinder consist of a first small cylinder in which the fourth piston is movable and a coaxial larger cylinder that contains another piston which is connected to said fourth piston; said larger cylinder being coaxial with a slightly smaller cylinder to which it is joined by a stepped portion, the first solenoid coil surrounding said slightly smaller cylinder with the first plunger being movable in said slightly smaller cylinder under the influence of said first solenoid coil, said another piston being biased against the stepped portion by a spring and separated from the first plunger by a gap.

7. An apparatus as defined in claim 6, wherein said another piston contains a cavity with a central opening facing said slightly smaller cylinder, the width of said central opening being smaller than the width of the cavity; an adjustment rod extending through said central opening into said slightly smaller cylinder and being attached to an enlarged base which is located in said cavity, the base having a width larger than said central opening with the rest position of the base in said cavity being adjustable by said rod, the side of the cavity containing said central opening in co-operation with said enlarged base acting as a stop to limit the distance through which said another piston can move when impacted by the first plunger.

8. An apparatus as defined in claim 7, wherein the first plunger is cylindrical with a central bore and said rod extends through the central bore of the first plunger, the rod being connected to an external micrometer adjustment mechanism which can adjust stroke through which said another piston can move.

9. An apparatus as defined in claim 1, wherein an attachment for filling the first cylinder with liquid medication consists of a thin hollow needle with an integral cap having an opening in communication with the hollow needle, the needle and cap being embedded in a cylindrical collet with the needle protruding from one end of the collet which has a central cylindrical opening co-axial with the needle and extending to the other end of the collet, the cap being located at an inner end of the cylindrical opening which is of a size in which the hand-held portion will fit.

10. An apparatus as defined in claim 9, wherein the outer surface of said one end of the collet is threaded and an internally threaded collet is threaded onto said one end; the collet which is threaded on its outer surface having flexible fingers around its circumference extending past said one end, the free end of the fingers having inwardly extending hooks which are biased inwardly to clamp around the rim of a bottle which contains liquid medication as the attachment is pressed against the rim with the needle penetrating a seal for that bottle.

11. An apparatus as defined in claim 1, wherein the second adjustable drive system consists of a rotary electrical motor connected to a transmission system that converts rotary motion to linear motion which is applied by a linear actuator to said third piston.

12. An apparatus as defined in claim 11, wherein the hydraulic fluid in said third cylinder is in communication with hydraulic fluid in a flexible tube which is attached to an inlet of a return flow check valve in a junction block with an outlet of the check valve being in communication with the high pressure flexible tube at a T-connection in the junction block.

13. An apparatus as defined in claim 12, wherein the check valve is provided with a manually operated device that can form a path allowing hydraulic fluid to flow from the high pressure flexible tube back into said third cylinder.

14. An apparatus as defined in claim 12, wherein the first high pressure intensifier consists of an additional piston in an additional cylinder whose outlet is connected to another inlet of said T-connection, a platform being attached to an additional piston rod associated with said additional piston and spaced a short distance from a weight attached to a drive rod of a solenoid whose supply current is adjustable to impact the weight against said platform with a predetermined adjustable force.

15. An apparatus as defined in claim 14, wherein the check valve is provided with a manual operated device that can form a path allowing hydraulic fluid to flow from the high pressure flexible tube back into said third cylinder.

16. An apparatus as defined in claim 14, wherein a power supply to said solenoid is adjustable to move said weight with a reciprocating motion to provide a series of impacts against said platform, a spring returning the platform to its rest position between impacts.

17. An apparatus as defined in claim 16, wherein the check valve is provided with a manual operated device that can form a path allowing hydraulic fluid to flow from the high pressure flexible tube back into said third cylinder.

18. An apparatus as defined in claim 14, wherein the additional cylinder is located in a first block having a recess portion in its surface surrounding the additional piston rod which is connected to said additional piston, the additional piston rod having an enlarged portion located in said recess portion, a cover with a central circular opening which is smaller than said enlarged portion being attached to said surface with the additional piston rod extending through said central circular opening to said platform, the cover and surface of said recess portion opposite said cover in co-operation with said enlarged portion form stops for the motion of the enlarged portion and limit the stroke of the additional piston in the additional cylinder.

19. An apparatus as defined in claim 18, wherein a power supply to said solenoid is adjustable to move said weight with a reciprocating motion to provide a series of impacts against said platform, a spring returning the platform to its rest position between impacts.

20. An apparatus as defined in claim 19, wherein said spring is located between the platform and the cover.

21. An apparatus as defined in claim 18, wherein the check valve is provided with a manual operated device that can form a path allowing hydraulic fluid to flow from the high pressure flexible tube back into said third cylinder.

* * * * *